US00PP10553P

United States Patent [19]

Meilland

[11] Patent Number: Plant 10,553

[45] Date of Patent: Aug. 18, 1998

[54] MINIATURE ROSE PLANT NAMED 'MEICAFLON'

[75] Inventor: Alain A. Meilland, Antibes, France

[73] Assignee: CP (Delaware), Inc., Wilmington, Del.

[21] Appl. No.: 904,436

[22] Filed: Jul. 31, 1997

[51] Int. Cl.[6] ..... A01H 5/00

[52] U.S. Cl. ..... Plt./9

[58] Field of Search ..... Plt./7.1, 9, 10

*Primary Examiner*—Howard J. Locker

*Attorney, Agent, or Firm*—Burns, Doane, Swecker & Mathis, L.L.P.

[57] ABSTRACT

A new and distinct variety of rose plant of the Miniature Class is provided which abundantly forms attractive Neyron Rose blossoms that display a radiant appearance. A hanging growth habit is exhibited that renders the plant well suited for growing outdoors in a hanging basket. The plant propagates well from cuttings. The blossoms possess no fragrance, and the foliage is glossy.

1 Drawing Sheet

SUMMARY OF THE INVENTION

The new variety of Miniature rose plant was created by artificial pollination wherein two parents were crossed which previously had been studied in the hope that they would contribute the desired characteristics. The female parent (i.e., the seed parent) of the new variety was 'The Fairy' variety (non-patented in the United States). The male parent (i.e., the pollen parent) of the new variety was the product of a cross between the 'Katharina Zeimet' variety (non-patented in the United States) and the 'Meijikatar' variety (U.S. Plant Pat. No. 4,682). The parentage of the new variety can be summarized as follows:

'The Fairy'×('Katharina Zeimet'×'Meijikatar')

The seeds resulting from the above pollination were sown and small plants were obtained which were physically and biologically different from each other. Selective study resulted in the identification of a single plant of the new variety.

It was found that the new variety of Miniature rose plant of the present invention possesses the following combination of characteristics:

(a) forms in abundance attractive blossoms that are radiant Neyron Rose in coloration,
(b) exhibits a hanging growth habit,
(c) forms glossy medium green foliage,
(d) propagates well on its own roots, and
(e) is particularly suited for growing as ornamentation in a hanging basket.

The new variety well meets the needs of the horticultural industry. It is particularly well-suited for use as attractive ornamentation when growing outdoors in a hanging pot.

The new variety has been found to undergo asexual propagation in France by a number of routes, including budding, grafting and cuttage. Asexual propagation by the above-mentioned methods as performed in France has shown that the characteristics of the new variety are strictly transmissible from one generation to another.

The new variety has been named the 'Meicaflon' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during November while growing on their own roots indoors at LeCannet des Maures, Var, France.

DETAILED DESCRIPTION

Figures 1, 2, 3, 4, 5, 6, 7, 8, 9, 10, 11, 12, 13, 14, 15, 16:
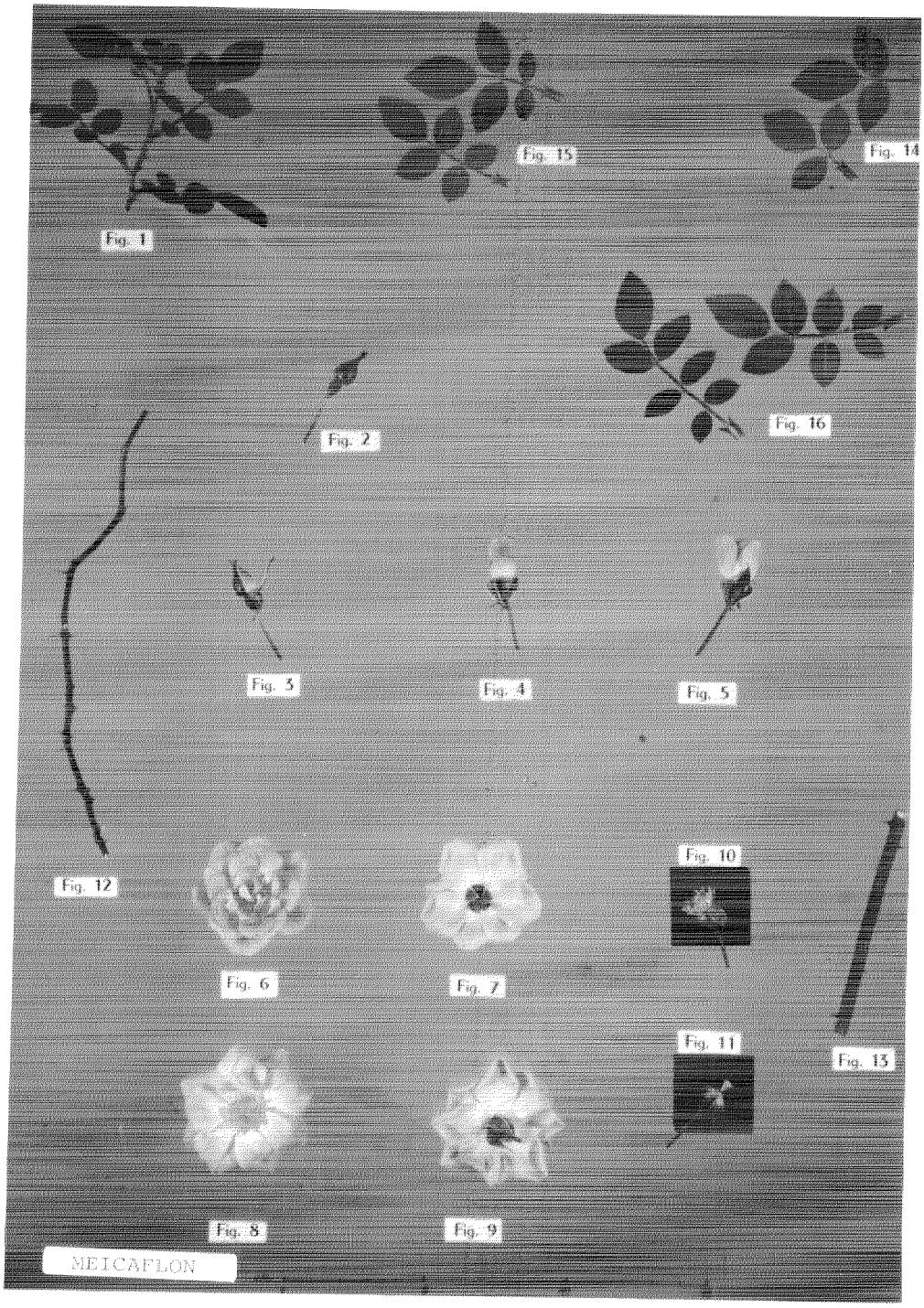
FIG. 1 illustrates a specimen of a young shoot.
FIG. 2 illustrates a specimen of a floral bud before the opening of the sepals.
FIG. 3 illustrates a specimen of a floral bud at the opening of the sepals.
FIG. 4 illustrates a specimen of a floral bud at the opening of the petals.
FIG. 5 illustrates a specimen of a flower during the course of opening.
FIG. 6 illustrates a specimen of an open flower— plan view— obverse.
FIG. 7 illustrates a specimen of an open flower— plan view— reverse.
FIG. 8 illustrates a specimen of a fully open flower—plan view— obverse.
FIG. 9 illustrates a specimen of a fully open flower—plan view— reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates specimens of leaves with three leaflets with the upper surface being shown at the top right and the under surface being shown at the bottom left.
FIG. 15 illustrates specimens of leaves with five leaflets with the upper surface being shown at the top right and the under surface being shown at the bottom left.
FIG. 16 illustrates specimens of leaves with seven leaflets with the upper surface being shown at the left and the under surface being shown at the right.

The chart used in the identification of the colors is that of The Royal Horticultural Society (R.H.S. Colour Chart). The terminology which preceds reference to the chart has been added to indicate the corresponding colors in more common terms. The description is based on two year-old specimens of the new variety which were observed during November while growing on *Rosa froebelli* understock indoors at LeCannet des Maures, Var, France.

Class: Miniature.

Plant:

*Height.*—Approximately 35 cm. on average at the end of the growing season.

*Habit.*—Hanging.

Branches:

Color.—Young stems: light green, green group 137D. Adult wood: medium green, green group 137B.

Thorns.—Size: small. Quantity: moderately numerous.

Leaves:

*Petioles.*—Upper surface: striped, reddish on young foliage and medium green on mature foliage with more or less glandular edges. Under surface: light green and bear some small thorns.

Stipules Adnate, pectinate, and linear.

Leaflets Number: 3, 5 (most often), and 7. Shape: elliptic. Texture: consistent. General appearance: very dense, and glossy foliage. Color (young foliage): Upper surface: medium green, green group 137C. Under surface: light green, green group 139C. Color (adult foliage): Upper surface: dark green, green group 137A. Under surface: medium green, green group 138B.

Inflorescence:

*Number of flowers.*—Commonly approximately 6 to 15 per stem in clusters.

*Peduncle.*—Light green and more or less tinted with reddish brown coloration, and the length is approximately 3 to 4 cm. on average.

*Sepals.*—Upper surface: tomentose, and greenish in coloration. Under surface: light green in coloration and commonly with weak extensions.

*Buds.*—Shape: conical. Length: Approximately 1.5 cm. on average. Size: small. Color upon opening: Upper surface: light rose bengal, red-purple group 57C. Under surface: neyron rose, red-purple group 58C.

*Flower.*—Form: flattened cup. Diameter: approximately 4 cm. on average. Color (when opening begins): Upper surface: light neyron rose, red group 55C with lighter outside petals. Under surface: light neyron rose, red group 55C with lighter outside petals. Color (when blooming): Under surface: light neyron rose, red group 55C with lighter outside petals and more or less suffused with medium neyron rose, red group 55B. Under surface: light neyron rose, red group 55C with lighter outside petals and more or less suffused with medium neyron rose, red group 55B. Color (at end of opening): Upper surface: light Neyron Rose, Red Group 55C with lighter outside petals and more or less suffused with medium neyron rose, red group 55B. Under surface: light neyron rose, red group 55C with lighter outside petals and more or less suffused with medium neyron rose, red group 55B. Fragrance: none. Petal number: approximately 25 on average. Petal shape: oval. Petal drop: good. Anthers: normal and ochre in coloration. Stamen number: approximately 72 on average. Filaments: greenish straw in coloration. Pistil number: approximately 58 on avreage. Stigmas: normal and greenish straw in coloration. Styles: greenish straw in coloration. Receptacle: medium green, and in longitudinal section in the shape of a pear.

Lasting quality: long on the plant.

Development:

*Vegetation.*—Very strong.

*Blooming.*—Very abundant.

*Resistance to diseases.*—Good.

*Aptitude to bear fruit.*—Good.

I claim:

1. A new and distinct variety of Miniature rose plant characterized by the following combination of characteristics:

(a) forms in abundance attractive blossoms that are radiant Neyron Rose in coloration,
(b) exhibits a hanging growth habit,
(c) forms glossy medium green foliage,
(d) propagates well on its own roots, and
(e) is particularly suited for growing as oramentation in a hanging basket;

substantially as herein shown and described.

* * * * *

MEICAFLON